United States Patent [19]

Ehmann

[11] 4,429,793
[45] Feb. 7, 1984

[54] DIABETIC TRAVELING CASE

[75] Inventor: Emil G. Ehmann, Kenilworth, N.J.

[73] Assignee: Ehmann Corporation, Kenilworth, N.J.

[21] Appl. No.: 377,850

[22] Filed: May 13, 1982

[51] Int. Cl.³ .................... A45C 11/20; B65D 69/00; F25D 3/08
[52] U.S. Cl. ................................. 206/570; 150/34; 206/366; 206/545; 206/571; 206/828
[58] Field of Search ............ 206/363, 570, 364, 571, 206/545, 828, 366, 823; 62/372; 150/34

[56] References Cited

U.S. PATENT DOCUMENTS

| | | | |
|---|---|---|---|
| 1,625,035 | 4/1927 | Lilly | 206/571 |
| 1,995,799 | 3/1935 | Doniger | 206/571 |
| 2,038,319 | 4/1936 | Stanley | 132/79 G |
| 2,167,926 | 8/1939 | Glasker | 150/34 |
| 2,804,969 | 9/1957 | Barnett | 150/34 |
| 3,148,515 | 9/1964 | Jenris et al. | 62/222 |
| 4,050,264 | 9/1977 | Tanaka | 62/457 |
| 4,250,998 | 2/1981 | Taylor | 206/570 |
| 4,368,819 | 1/1983 | Durham | 206/545 |

FOREIGN PATENT DOCUMENTS 1092456 11/1967 United Kingdom .................. 150/34

Primary Examiner—William T. Dixson, Jr.
Assistant Examiner—Brenda J. Ehrhardt
Attorney, Agent, or Firm—Lerner, David, Littenberg, Krumholz & Mentlik

[57] ABSTRACT

A diabetic traveling case is compact enough to be pocket-sized. The pocket-sized case is equipped to carry at least one bottle of insulin, as well as a refrigerant which maintains the insulin at a suitably low temperature to avoid spoiling.

4 Claims, 1 Drawing Figure

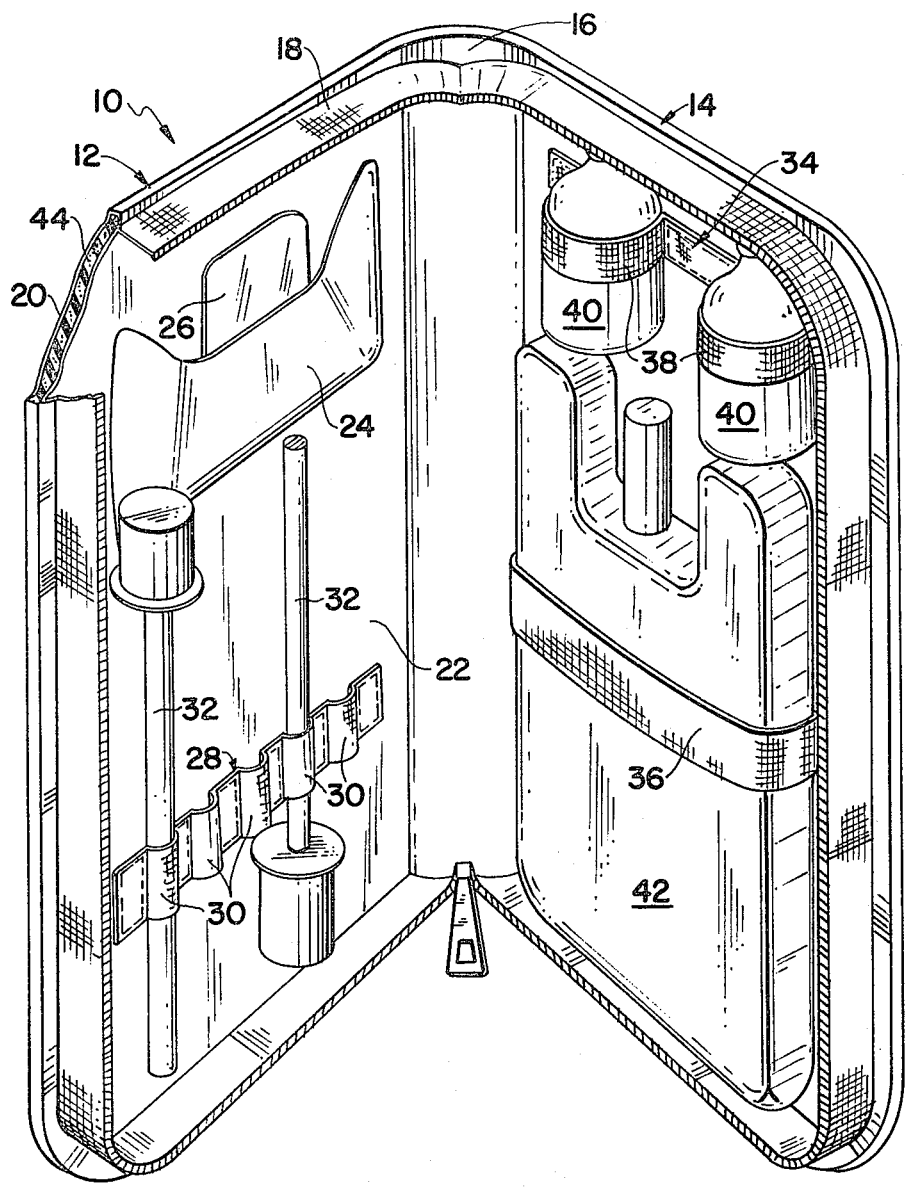

DIABETIC TRAVELING CASE

FIELD OF THE INVENTION

The present invention relates to a diabetic traveling case, and, more particularly, such a case which is compact enough to be pocket-sized.

BACKGROUND ON THE INVENTION

Portable refrigerated insulin traveling kits have been known for many years (see, for instance, U.S. Pat. Nos. 3,148,515 and 4,250,998). Although these prior art kits are portable, they are not compact enough to be carried in jacket pockets, pants pockets and pocketbooks. Thus, these devices can be rather conspicuous.

A pocket-sized insulin traveling kit is also known. However, the compactness of this prior art kit is achieved at the expense of providing a refrigerant for maintaining the insulin at a suitably low temperature. Thus, this kit has only limited utility.

SUMMARY OF THE INVENTION

The present invention relates to a new and improved diabetic traveling case which is compact enough to be pocket-sized. The pocket-sized diabetic traveling case includes a first cover, which has an inner surface and an outer surface, and a second cover, which also has an inner surface and an outer surface. The covers can be pivoted relative to each other between a closed position in which they are arranged parallel to each other with their inner surfaces in face-to-face relationship and an open position in which they are pivoted away from each other. One or more insulin containers can be releasably attached to the inner surface of one of the covers by, for instance, an elastic strap. A cooling medium, such as a substantially flat container of a freezing material, can also be attached to the inner surface of one of the covers such that the cooling medium is in close proximity to the insulin container or containers when the covers are in their closed position. Because of the proximity of the cooling medium to the insulin container or containers, the insulin is maintained at a suitably low temperature when the covers are in their closed position.

In one embodiment, the insulin container or containers and the cooling medium are attached to the same cover of the pocket-sized traveling case. The other cover can then be used to hold syringes and other miscellaneous items, such as alcohol swabs and Band-Aids, which are commonly used by a diabetic.

BRIEF DESCRIPTION OF THE DRAWING

For a more complete understanding of the present invention, reference may be had to the following detailed description of exemplary embodiment taken in conjunction with the accompanying drawing in which the sole FIGURE is a perspective view of a diabetic traveling case constructed in accordance with the present invention, the traveling case being shown in an open position with one corner broken away to facilitate consideration and discussion.

DESCRIPTION OF THE EXEMPLARY EMBODIMENT

Referring to the sole FIGURE of the drawing, there is shown a pocket-sized diabetic traveling case 10 which includes a front cover 12 and a back cover 14. A center binder 16 pivotally attaches the covers 12, 14 to each other. A wide-band zipper 18 is also provided for opening and closing the case 10. The case 10 has an outer covering 20 made from any suitable material, such as real or simulated leather, and an inner covering 22 made, for example, from a water resistant plastic.

The inside of the front cover 12 is provided with a pouch 24 adapted to hold a package of alcohol swabs or wipes 26. The pouch 24 could also be employed to hold Band-Aids and other items used by a diabetic. An elastic strap 28 is also stitched to the inside of the front cover 12. The elastic strap 28 is stitched so as to form five loops 30, each of which has a size and shape such that it can resiliently and releasably receive a syringe 32.

The inside of the back cover 14 is provided with a pair of elastic straps 34, 36. The upper strap 34 is stitched so as to form a pair of loops 38, each of which resiliently and releasably receives an insulin bottle 40. The insulin bottles 40 may contain the same type of insulin or one bottle may contain R-type insulin while the other bottle contains N-type insulin. The lower strap 36 resiliently and releasably holds a substantially flat plastic container 42 of freezing material, such as "Blue Ice". The container 42 is positioned in close proximity to the insulin bottles 40 so that the insulin will stay sufficiently cool to prevent spoiling.

In order to keep the inside of the case 10 as cool as possible for as long as possible, thermal insulation 44 is provided between the outer and inner coverings 20, 22, respectively, of the case 10. The thermal insulation 44 may be of any suitable type, such as Styrofoam (i.e., expanded cellular polystyrene).

The front and back covers 12,14, respectively are approximately 4" wide and 7¾" long. The center binder 16 is approximately 1¾" wide and 7¾" long. Thus, when the case 10 is closed, it has a length of about 7¾", a width of about 4" and a thickness of about 1¾". These dimensions make the case 10 compact enough so that it can be carried in jacket pockets, certain pants pockets and pocketbooks.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

We claim:

1. A pocket-sized diabetic traveling case, comprising a first cover, having an inner surface, an outer surface and a layer of expanded cellular polystyrene sandwiched between said inner and outer surfaces of said first cover so as to thermally insulate said first cover; a second cover, having an inner surface, an outer surface and a layer of expanded cellular polystyrene sandwiched between said inner and outer surfaces of said second cover so as to thermally insulate said second cover; connecting means for pivotally connecting said first and second covers to each other such that said first and second covers are pivotal relative to each other between a closed position in which said first and second covers are arranged parallel to each other with said inner surfaces thereof in face-to-face relationship and an open position in which said first and second covers are pivoted away from each other; first attaching means releaseably attaching at least two insulin containers to said inner surface of said first cover, said first attaching means including an elastic strap having a plurality of loops formed therein, each loop being sized and shaped so as to releaseably receive one of said insulin containers; second attaching means releaseably attaching a substantially flat container of freezing material to said inner surface of said first cover such that said container of freezing material is in close proximity to said insulin containers, whereby said insulin containers are refrigerated by said container of freezing material when said first and second covers are in at least said closed position; first holding means for releaseably holding a plurality of syringes, said first holding means including an elastic strap attached to said inner surface of said second cover and having a plurality of loops formed therein, each loop being sized and shaped so as to releaseably receive one of said syringes; second holding means for releaseably holding miscellaneous items, such as alcohol swabs, said second holding means including a pouch attached to said inner surface of said second cover; and a zipper attached to said first and second covers so as to releaseably maintain said first and second covers in said closed position.

2. A pocket-sized diabetic traveling case according to claim 1, wherein said connecting means is a binder connected between said first and second covers.

3. A pocket-sized diabetic traveling case according to claim 1, wherein said case has a length of about 7¾", a width of about 4" and a thickness of about 1¾" when said first and second covers are in said closed position.

4. A pocket-sized diabetic traveling case according to claim 1, wherein said first and second attaching means are arranged one above the other.

* * * * *